US012227433B2

(12) United States Patent
Cader et al.

(10) Patent No.: US 12,227,433 B2
(45) Date of Patent: Feb. 18, 2025

(54) ELECTRICAL FREQUENCY RESPONSE FLUID ANALYSIS (71) Applicant: Hewlett Packard Enterprise Development LP, Houston, TX (US)

(72) Inventors: Tahir Cader, Liberty Lake, WA (US); Greg Scott Long, Corvallis, OR (US); John Franz, Houston, TX (US); Gardson Githu, Los Angeles, CA (US)

(73) Assignee: Hewlett Packard Enterprise Development LP, Spring, TX (US)

( * ) Notice: Subject to any disclaimer, the term of this patent is extended or adjusted under 35 U.S.C. 154(b) by 668 days.

(21) Appl. No.: 15/569,650

(22) PCT Filed: Feb. 19, 2016

(86) PCT No.: PCT/US2016/018681
§ 371 (c)(1),
(2) Date: Oct. 26, 2017

(87) PCT Pub. No.: WO2017/142553
PCT Pub. Date: Aug. 24, 2017

(65) Prior Publication Data
US 2018/0111846 A1    Apr. 26, 2018

(51) Int. Cl.
*G01N 27/02* (2006.01)
*A61L 2/18* (2006.01)
(Continued)

(52) U.S. Cl.
CPC ............... *C02F 1/008* (2013.01); *A61L 2/18* (2013.01); *A61L 2/186* (2013.01); *G01N 27/026* (2013.01);
(Continued)

(58) Field of Classification Search
CPC .... C02F 1/008; C02F 1/50; C02F 1/66; C02F 1/46–4602; C02F 1/461–46109;
(Continued)

(56) References Cited

U.S. PATENT DOCUMENTS 4,244,800 A    1/1981 Frazzini
4,737,465 A    4/1988 Bond
(Continued)

FOREIGN PATENT DOCUMENTS

CN    102356454 A    2/2012
CN    103917863 A    7/2014
(Continued)

OTHER PUBLICATIONS

Supplementary Partial European Search Report and Search Opinion Received for EP Application No. 16890848.1, mailed on Dec. 11, 2018, 13 pages.
(Continued)

*Primary Examiner* — Luan V Van
*Assistant Examiner* — Vivian A Tran
(74) *Attorney, Agent, or Firm* — Hewlett Packard Enterprise Patent Department (57) ABSTRACT In the examples provided herein, a system includes an electrochemical sensor having two electrodes inserted in a fluid to be tested, where an alternative current (AC) voltage is applied across the two electrodes; an electrochemical sensor having two electrodes inserted in a fluid to be tested, wherein an alternative current (AC) voltage across the two electrodes; and a frequency response analyzer to analyze the measured the electrical response across multiple frequencies. The system also includes a memory to store a baseline of the electrical response across multiple frequencies, and a processor to determine from the stored baseline and the
(Continued)

measured electrical response whether the electrical response is outside a predetermined range.

7 Claims, 9 Drawing Sheets

(51) Int. Cl.
*C02F 1/00* (2023.01)
*G01N 33/18* (2006.01)
*C02F 1/50* (2023.01)
*C02F 1/66* (2023.01)
*C02F 103/02* (2006.01)
*G01N 27/416* (2006.01)

(52) U.S. Cl.
CPC .......... *G01N 33/18* (2013.01); *A61L 2202/14* (2013.01); *C02F 1/50* (2013.01); *C02F 1/66* (2013.01); *C02F 2103/023* (2013.01); *C02F 2209/005* (2013.01); *C02F 2209/06* (2013.01); *C02F 2303/04* (2013.01); *C02F 2303/08* (2013.01); *G01N 27/4167* (2013.01)

(58) Field of Classification Search
CPC ...... C02F 1/469–4698; C02F 2103/023; C02F 2209/06; C02F 2303/04; C02F 2303/08; C02F 2209/005; A61L 2/18; A61L 2/186; A61L 2202/14; G01N 27/026; G01N 27/02–028; G01N 27/4163–4165; G01N 33/18; G01N 27/4167
See application file for complete search history.

(56) References Cited

U.S. PATENT DOCUMENTS

| | | | | |
|---|---|---|---|---|
| 4,853,638 A * | 8/1989 | Endou | .................... | G01N 27/06 324/441 |
| 5,448,178 A * | 9/1995 | Chen | .................... | G01N 17/02 204/404 |
| 6,238,555 B1 * | 5/2001 | Silveri | .................... | C02F 1/008 210/143 |
| 7,043,402 B2 | 5/2006 | Phillips | | |
| 7,581,434 B1 | 9/2009 | Discenzo | | |
| 7,838,281 B2 | 11/2010 | Kraus | | |
| 10,871,481 B2 | 12/2020 | Rogacs et al. | | |
| 2002/0125899 A1 * | 9/2002 | Lvovich | .................... | G01N 33/2888 324/698 |
| 2003/0222656 A1 * | 12/2003 | Phillips | .................... | G01N 27/02 324/605 |
| 2004/0108224 A1 | 6/2004 | Robertson | | |
| 2004/0262168 A1 * | 12/2004 | Huo | .................... | C25F 3/02 205/676 |
| 2005/0179449 A1 * | 8/2005 | Wooton | .................... | G01N 33/2888 324/691 |
| 2006/0127622 A1 * | 6/2006 | Mohan | .................... | F16L 58/10 428/36.91 |
| 2006/0178495 A1 * | 8/2006 | van Ooij | .................... | C09D 183/08 528/38 |
| 2008/0081120 A1 * | 4/2008 | Van Ooij | .................... | C09D 5/002 427/387 |
| 2009/0095643 A1 | 4/2009 | Svetlicic | | |
| 2011/0108439 A1 * | 5/2011 | Gourishankar | .... | G01N 27/4166 205/789 |
| 2011/0225997 A1 | 9/2011 | Gast | | |
| 2012/0006790 A1 | 1/2012 | Komori et al. | | |
| 2013/0214797 A1 * | 8/2013 | Gruden | .................... | D06F 39/004 324/663 |
| 2014/0251583 A1 | 9/2014 | Eriksen | | |
| 2014/0326340 A1 * | 11/2014 | Kuriki | .................... | C23F 11/18 137/565.11 |
| 2015/0115983 A1 | 4/2015 | Potyrailo et al. | | |
| 2015/0376420 A1 * | 12/2015 | Hintze-Bruning | ....... | C09D 7/70 428/457 |
| 2018/0348140 A1 * | 12/2018 | Quint | .................... | G01N 35/00623 |

FOREIGN PATENT DOCUMENTS

| | | | |
|---|---|---|---|
| CN | 104458867 A | * | 3/2015 |
| CN | 107209139 A | | 9/2017 |
| WO | 2016/122667 A1 | | 8/2016 |

OTHER PUBLICATIONS

International Search Report and Written Opinion received for PCT Patent Application No. PCT/US2016/018681, mailed on Nov. 11, 2016, 11 pages.
International Preliminary Report on Patentability received for PCT Patent Application No. PCT/US2016/018681, mailed on Aug. 30, 2018, 10 pages.
Polk B J et al: "Ag/Agcl microelectrodes with improved stability for microfluidics", Sensors and Actuators B: Chemical, Elsvier BV, NL, vol. 114, No. 1, Mar. 30, 2006 (Mar. 30, 2006), pp. 239-247.
JohnTech, "Leak Detection", available online at <http://www.johntech.com/infrastructure/monitoringsystems/leak-detection/>, Feb. 25, 2013, 6 pages.

* cited by examiner

ELECTRICAL FREQUENCY RESPONSE FLUID ANALYSIS

BACKGROUND

Closed loop water systems may be used as part of a cooling system. Lack of a proper water treatment program for closed systems leads to system corrosion, deterioration of components, and loss of heat transfer efficiency.

BRIEF DESCRIPTION OF THE DRAWINGS

The accompanying drawings illustrate various examples of the principles described below. The examples and drawings are illustrative rather than limiting.

DETAILED DESCRIPTION

In the past, closed loop cooling systems may have been designed without water treatment programs because of a common misconception that water treatment is applicable solely to open water cooling systems. However, cooling water used in a closed loop system should be properly treated to prevent system corrosion, deterioration of components, and loss of heat transfer efficiency. Filtered and de-mineralized water that comes in contact with wetted surfaces of the loop that carries the cooling water should be used, such as reverse osmosis water or deionized water. In addition, chemicals may be added to the water, such as corrosion inhibitors, for example, sodium silicate, sodium hexametaphosphate, and/or a molybdate-based corrosion inhibitor. Further, chemicals may be added to prevent and slow bacterial growth, such as isothiazalone, DBNPA (2,2-dibromo-3-nitrilopropionamide) biocide, and/or hydrogen peroxide silver biocide. Other chemicals may also be used in the cooling water for other purposes, such as adjusting the pH of the cooling water.

With previous systems, concentrations of various chemicals added to the water was measured manually by a technician who sampled the water and either performed on-site measurements or sent samples of the water to a testing laboratory. After chemical analysis results were received from the testing laboratory, if any of the chemicals were not within a predetermined range, the technician manually added the appropriate chemicals to re-balance the system. This type of monitoring and adjustment system is expensive and time consuming. Moreover, if poor system heat transfer performance is detected by system operators between intervals of water sampling testing, irreversible damage may occur to the system.

As described below, an electrochemical sensor may be used to automatically measure the electrical response of the cooling water in real-time to an applied AC voltage, where the electrical response is correlated to the concentration levels of chemicals in the water. Further, if any of the chemicals are not within a predetermined range, appropriate chemicals may be automatically added to the cooling water to re-balance the chemistry. The solution described below eliminates manual testing of the water chemistry, increases the accuracy of water chemistry maintenance, and reduces the cost of the water chemistry maintenance.

Figure 1A:
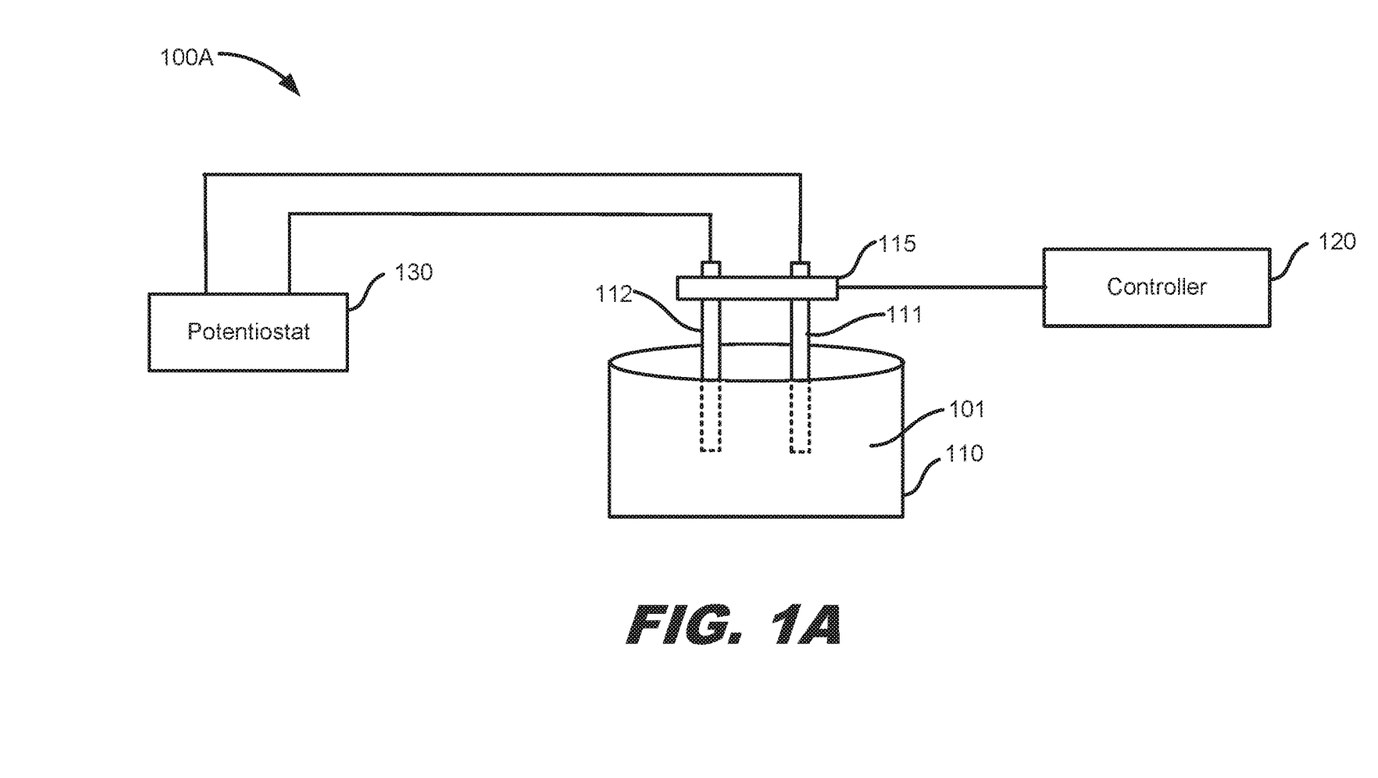
FIG. 1A depicts a diagram of an example electrochemical sensing device.

FIG. 1A depicts a diagram of an example electrochemical sensing device 100A capable of performing electrochemical impedance spectroscopy (EIS). The electrochemical sensing device 100A includes a sensor having a first electrode 111 and a second electrode 112; and a potentiostat 130. The first electrode 111 and the second electrode 112 are coupled to the potentiostat 130. A spacing between the first electrode 111 and the second electrode 112 may be adjustable by a controller 120. For example, in some implementations, one or both of the first and second electrodes 111, 112 may be coupled to a translation stage 115 controlled by the controller 120 that adjusts the spacing. Additionally, a depth at which the first electrode 111 and the second electrode 112 are inserted into a fluid 101 to be tested is also adjustable by the controller 120. For example, in some implementations, the first and second electrodes 111, 112 may be coupled to a translation stage 115 that adjusts a depth that the first and second electrodes 111, 112 are inserted into an enclosure 110 holding the fluid 101.

An alternating current (AC) voltage is applied across the electrodes 111, 112 by the potentiostat 130, and the resultant electrical response across the first and second electrodes via the fluid is measured, such as complex impedance. The potentiostat 130 may apply the AC voltage at various different frequencies, and the response across the electrodes 111, 112 at the different frequencies is measured. The electrical response may be determined by measuring a magnitude of a resultant current, and the phase difference between the current and voltage waveforms may be used to determine the real and imaginary components of the impedance across the fluid. By taking measurements at different electrical frequencies, a spectrum vector of frequency-impedance pairs may be obtained. Alternatively, differentiation between components in the fluid may be performed by selecting the appropriate frequency ranges for analysis. The electrical response corresponds to any one or more of the pH and concentration of a single or multiple chemicals in the fluid. In some implementations, the chemicals may include an acidic or alkaline solution, a biocide and/or a corrosion inhibitor.

Figure 1B:
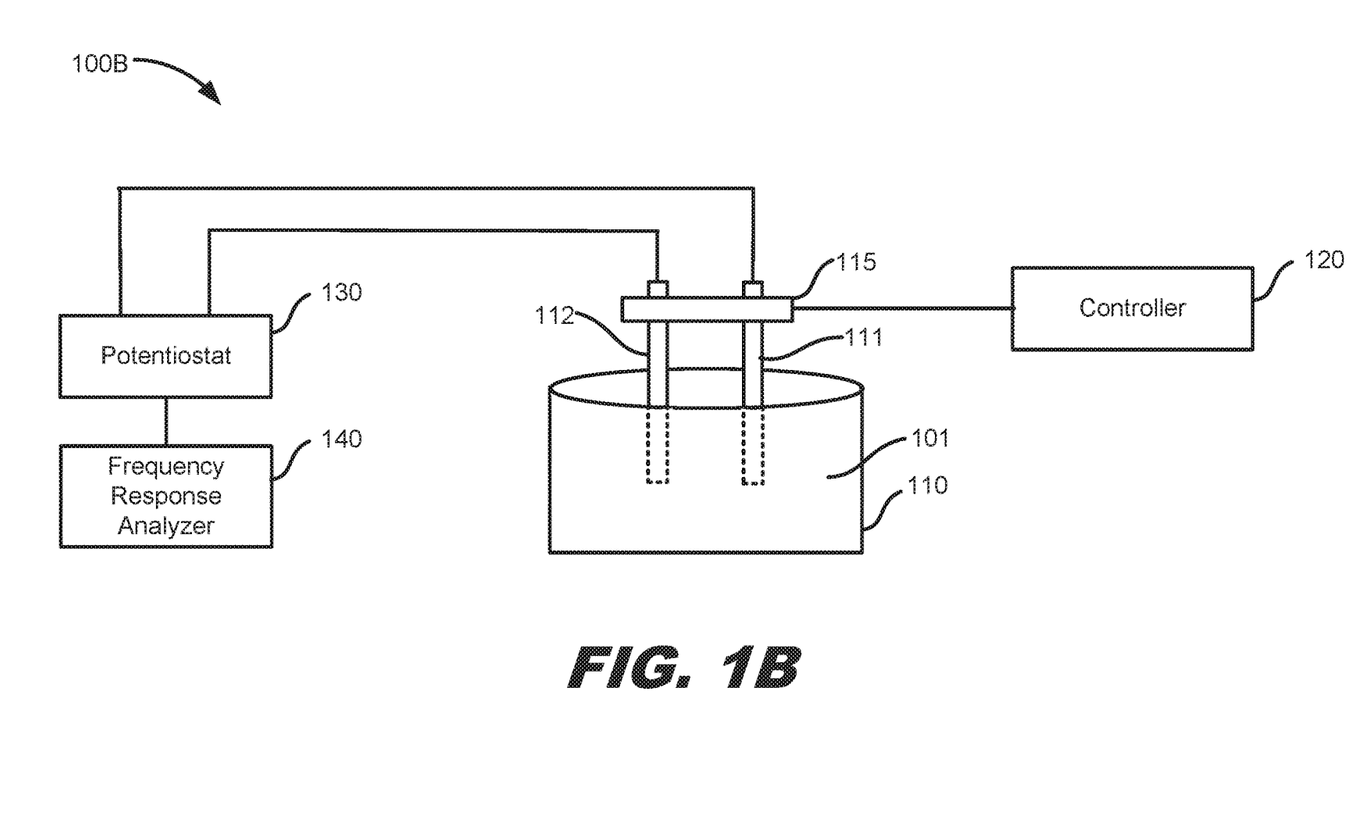
FIG. 1B depicts a diagram of another example electrochemical sensing device.

FIG. 1B depicts a diagram of another example electrochemical sensing device 100B. The electrochemical sensing device 100B is similar to sensing device 100A depicted in FIG. 1A but also includes a frequency response analyzer 140. The frequency response analyzer 140 is coupled to the potentiostat 130 and analyzes the electrical response across the first and second electrodes 111, 112 via the fluid at multiple electrical frequencies.

In some implementations, the frequency response analyzer 140 may store data, including a baseline spectrum of an electrical response measured by the potentiostat 130 when the electrodes 111, 112 are inserted in reverse osmosis (RO) water or deionized (DI) water, as RO water and DI water are used in cooling facility water loops. The cooling facility water loop is distinct from the information technology (IT) water loop, where water in the IT water loop flows directly into the racks and servers. The frequency response analyzer 140 may also store a baseline spectrum of the electrical response when the electrodes 111, 112 are inserted in RO or DI water with appropriate amounts of each individual chemical used to adjust the chemistry of the fluid used in the cooling system. Additionally, the frequency response analyzer 140 may store a baseline spectrum of the electrical response when the electrodes 111, 112 are inserted in the fluid when appropriate amounts of all the chemicals to be added to the RO or DI water to obtain the desired final chemistry for the fluid.

Alternatively, the data may be stored in a memory (not shown) that is accessible by the frequency response analyzer 140.

In some implementations, the frequency response analyzer 140 may determine from the stored baseline spectra and the measured electrical response whether the electrical response is outside a predetermined range. For example, if it is determined that the complex impedance is below a threshold level at a particular frequency or group of frequencies, a first chemical or diluting RO water or DI water may be added. If it is determined that the complex impedance is above a maximum level at the particular frequency or group of frequencies, a different chemical or RO water or DI water may be added.

In some implementations, the fluid to be tested is used in a closed loop cooling system, such as used in cooling computer room air handlers or computer room air conditioners in a data center.

Figure 2A:
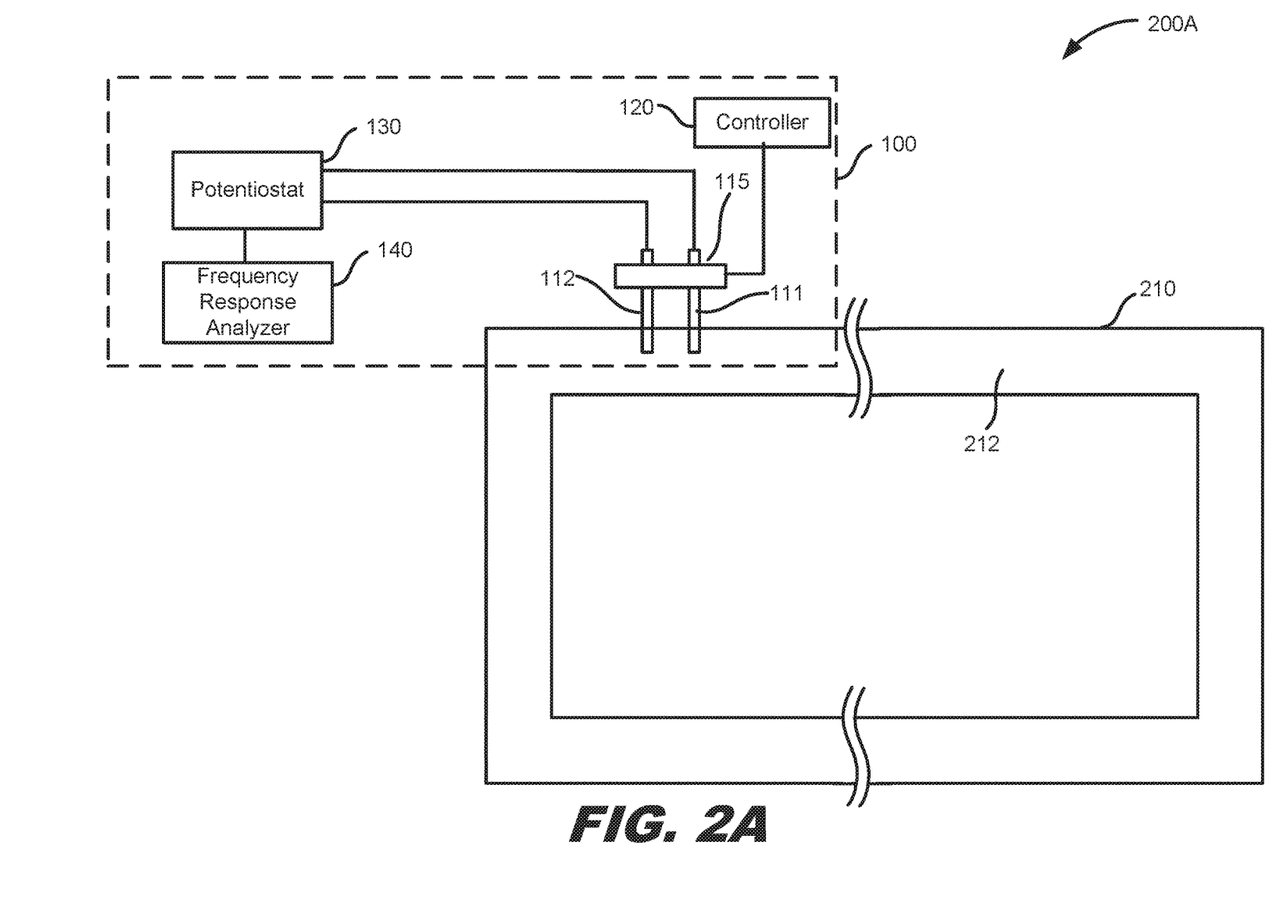
FIG. 2A depicts a diagram of an example system that determines whether a chemistry of a fluid is to be adjusted.

FIG. 2A depicts a diagram of an example system 200A that determines whether a chemistry of a fluid is to be adjusted. The system includes an electrochemical sensing device 100B as described in FIG. 1B that is used to test cooling fluid 212 in a cooling loop 210. While a single electrochemical sensor is shown in FIG. 2A, any number of electrochemical sensors may be used. In some implementations, one of the sensors may be placed in a coolant distribution unit where additives are mixed-in to the fluid of the cooling loop 210. In some implementations, multiple sensors may be coupled to a single potentiostat 130 or a single frequency response analyzer 140.

The two electrodes 111, 112 of the sensor 100 are inserted in a fluid 212 to be tested in a closed loop system 210. In some implementations, the closed loop cooling system 210 may be used, for example, to cool computer room air handlers or computer room air conditioners in a secondary loop in a data center.

Figure 3:
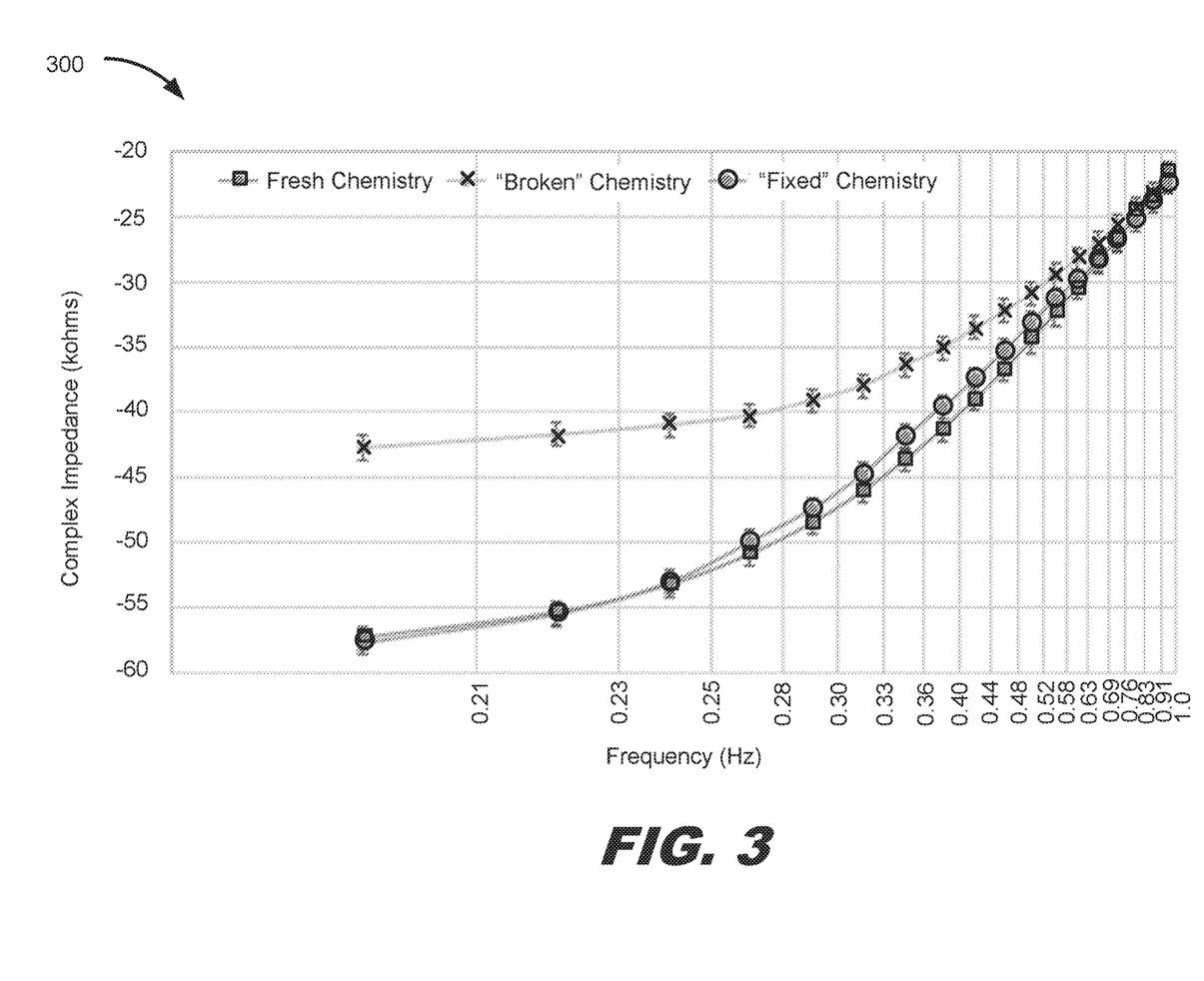
FIG. 3 depicts a graph of example complex impedance measurements as a function of frequency for different cooling fluid chemistries.

FIG. 3 depicts a graph of example complex impedance measurements as a function of frequency for different cooling fluid chemistries. In the example of FIG. 3, a baseline impedance spectrum for a cooling fluid with a desired chemistry is indicated by the line with square data points. The pH level of the cooling fluid was intentionally changed by injecting a dilute acid into the fluid, resulting in the impedance spectrum having data points identified by an 'x,' also shown in FIG. 3. Subsequently, the pH level of the cooling fluid was restored to the desired level by injecting a dilute alkaline solution into the cooling fluid. The resulting impedance spectra is shown in FIG. 3 by the line with the circular data points, which is nearly the same as the baseline spectra, within measurement error. Thus, the measured complex impedance spectrum of the cooling fluid may be used as an indicator of whether the pH level of a fluid is within a desired range. Experiments have also shown that the measured complex impedance spectrum may also be used as an indicator of whether a corrosion inhibitor or biocide level in the cooling fluid are each within their respective desired ranges.

Figure 4:
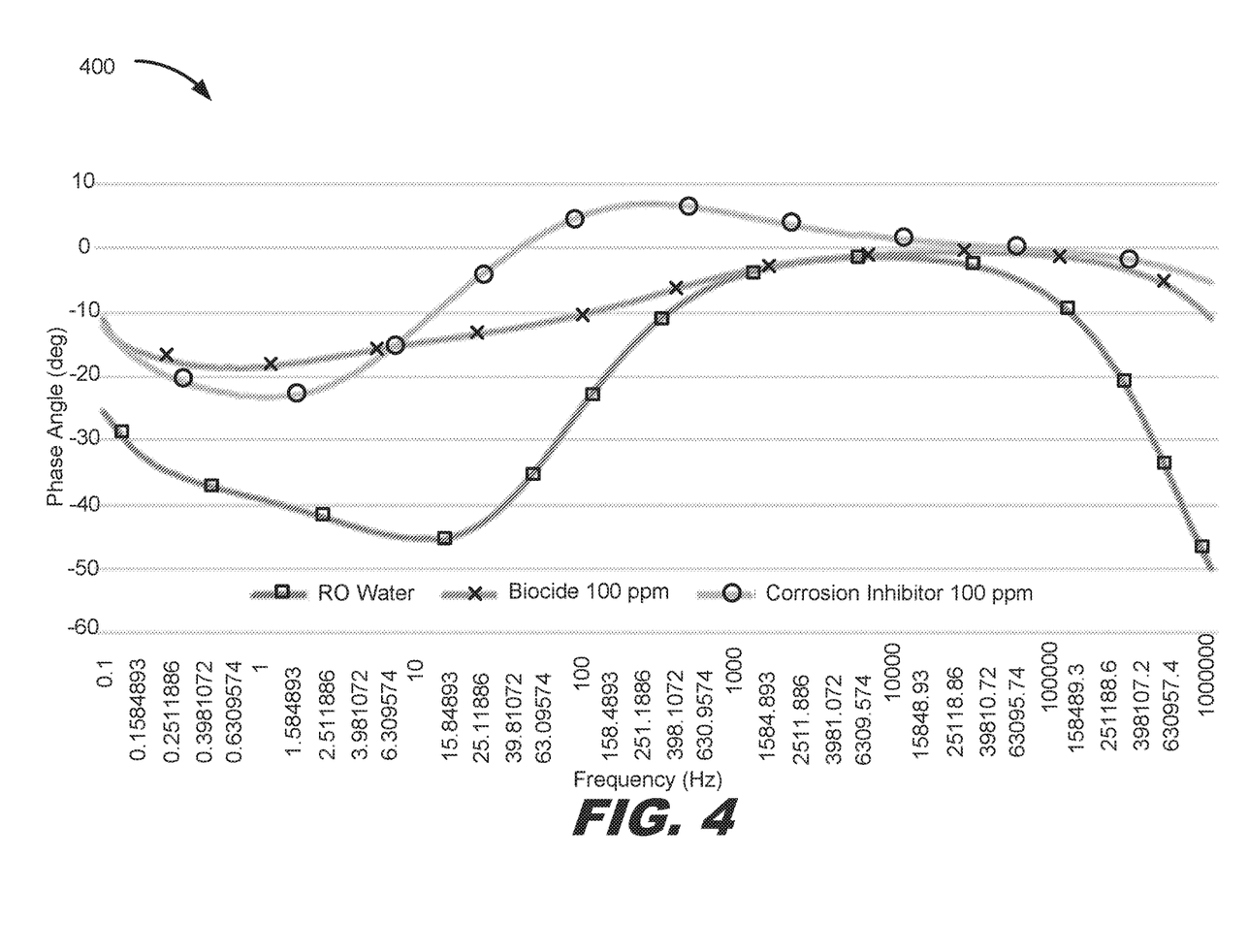
FIG. 4 depicts a graph of example phase angle difference measurements between a measured current waveform and an applied voltage waveform as a function of frequency for different cooling fluid chemistries.

FIG. 4 depicts a graph of example phase angle difference measurements between a measured current waveform and an applied voltage waveform as a function of frequency for different cooling fluid chemistries. In the example of FIG. 4, a baseline spectrum for the phase angle difference for RO water with no added chemicals is shown by the line with square-shaped data points. When 100 parts per million (ppm) of a biocide is added to the RO water, the resulting phase angle difference spectrum is indicated by the line with the 'x'-shaped data points. Also, when 100 ppm of a corrosion inhibitor is added to the RO water, the resulting phase angle difference spectrum is shown by the line with the circle-shaped data points.

By using these spectra, it is possible to determine how much of which particular additives is outside a predetermined desired range for each additive. For example, in FIG. 4, at an applied electrical frequency of 15.8 Hz, the phase angle difference between a measured current waveform and an applied voltage for RO water is approximately −45 degrees, while the phase angle difference for RO water with added biocide is approximately −13 degrees, and the phase angle difference for RO water with added corrosion inhibitor is approximately 8 degrees. By using the phase angle difference at multiple frequencies, the contribution of biocide and corrosion inhibitor can be determined for a particular state of the chemistry. Further, an appropriate amount of chemical additives to be added to restore the cooling fluid to the proper concentration levels of the additives may be determined in advance for different states and stored in the frequency response analyzer 140 or another memory accessible by the frequency response analyzer 140. This information may be stored as a lookup table, in some other type of database, or as a parametric relationship.

Figure 2B:
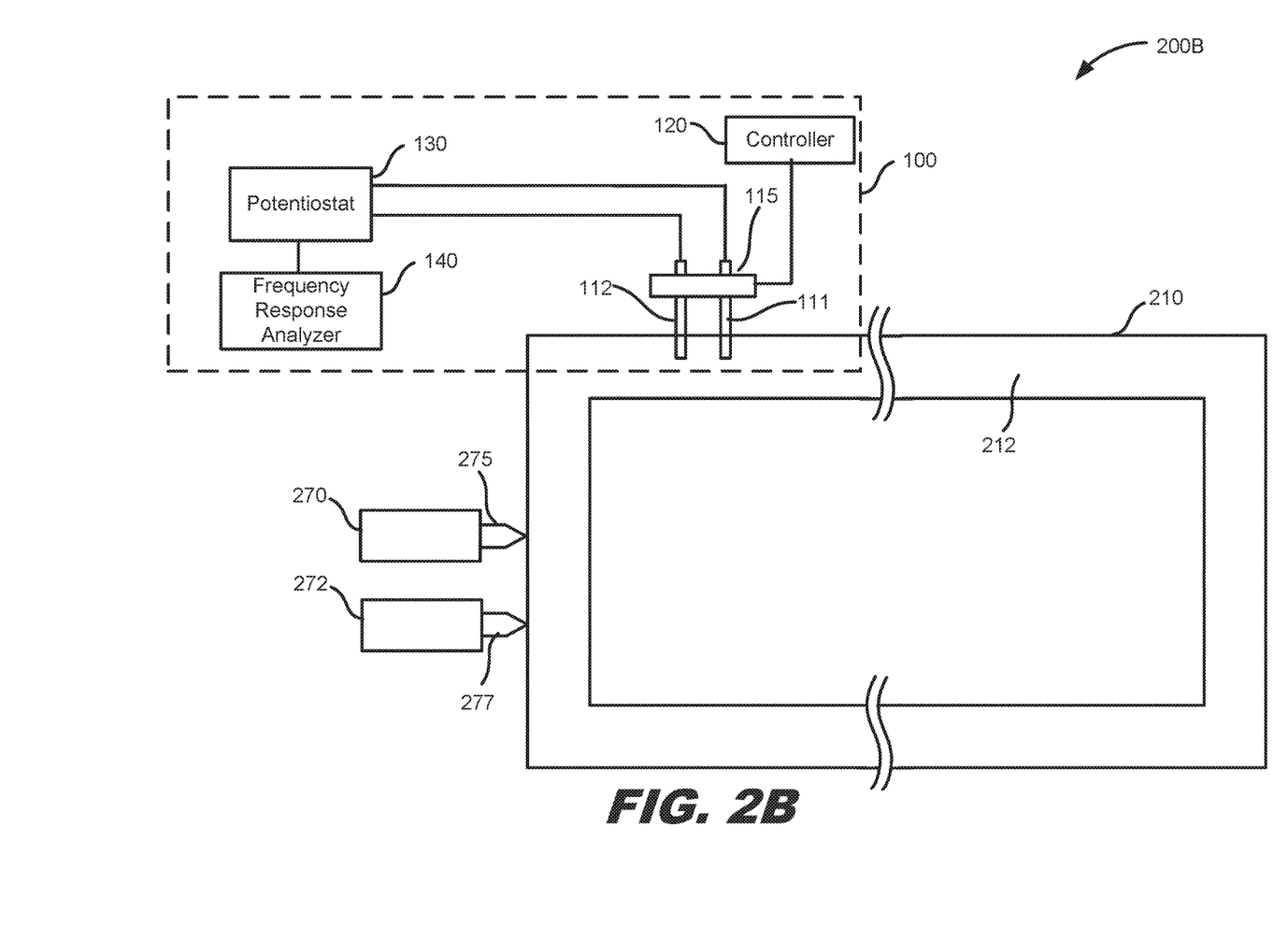
FIG. 2B depicts a diagram of another example system that determines whether a chemistry of a fluid is to be adjusted.

The system may also be able to automatically add the corrective additives to correct the chemistry of the fluid and return it to the appropriate state without manual intervention. FIG. 2B depicts a diagram of another example system 200B that determines whether a chemistry of a fluid is to be adjusted. The system 200B includes the elements of system 200A described above and also includes a first reservoir 270 containing a first chemical, RO water, or DI water; a first injector 275; a second reservoir 272 containing a second chemical, RO water, or DI water; and a second injector 277. The first injector may be controlled by the frequency response analyzer 140 or another processor to automatically inject a first amount of the contents of the first reservoir 270 into the fluid 212 if the electrical response at particular frequencies is above a predetermined range. The second injector is controlled by the frequency response analyzer 140 or another processor to automatically inject a second amount of the contents of the second reservoir 272 into the fluid if the electrical response at particular frequencies is below the predetermined range. While two reservoirs are shown in the example of FIG. 2B, any number of different reservoirs having different contents may be used, along with corresponding injectors to enable correction of concentration levels of different chemicals and/or the pH of the fluid.

Figure 5:
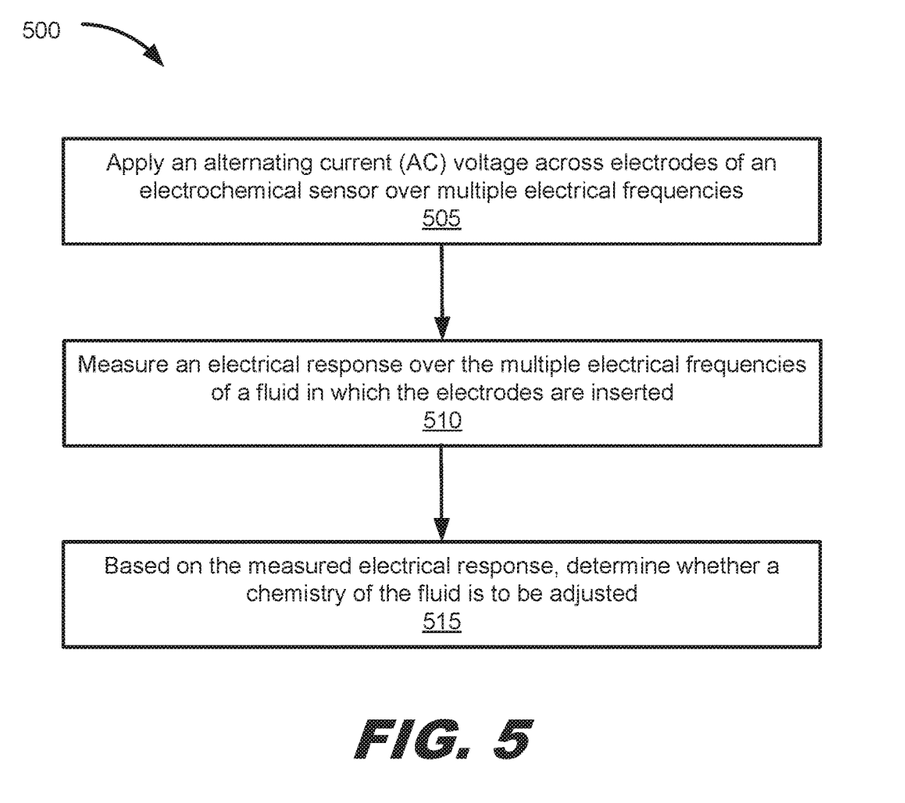
FIG. 5 depicts a flow diagram illustrating an example process of determining whether a chemistry of a fluid is to be adjusted.

FIG. 5 depicts a flow diagram illustrating an example process 500 of determining whether a chemistry of the fluid is to be adjusted.

The process begins at block 505, where an alternating current (AC) voltage may be applied across electrodes of an electrochemical sensor by a potentiostat. The AC voltage is applied over multiple electrical frequencies.

At block 510, an electrical response of a fluid in which the electrodes are inserted may be measured by the potentiostat. The measurements are performed over the multiple electrical frequencies at which the AC voltage is applied.

At block 515, based on the measured frequency response, it may be determined by a frequency response analyzer or other processor whether a chemistry of the fluid is to be adjusted. In some implementations, the electrical response may include at least one of a complex impedance and a phase angle difference between a current waveform and a voltage waveform. For example, if the electrical response of the fluid is measured to have a greater complex impedance than expected, a predetermined chemical may be added to the fluid. The amount of chemical may be dependent upon the difference between the measured complex impedance and the expected complex impedance at a given electrical frequency. In some implementations, the fluid may be used in a closed loop cooling system.

Figure 6:
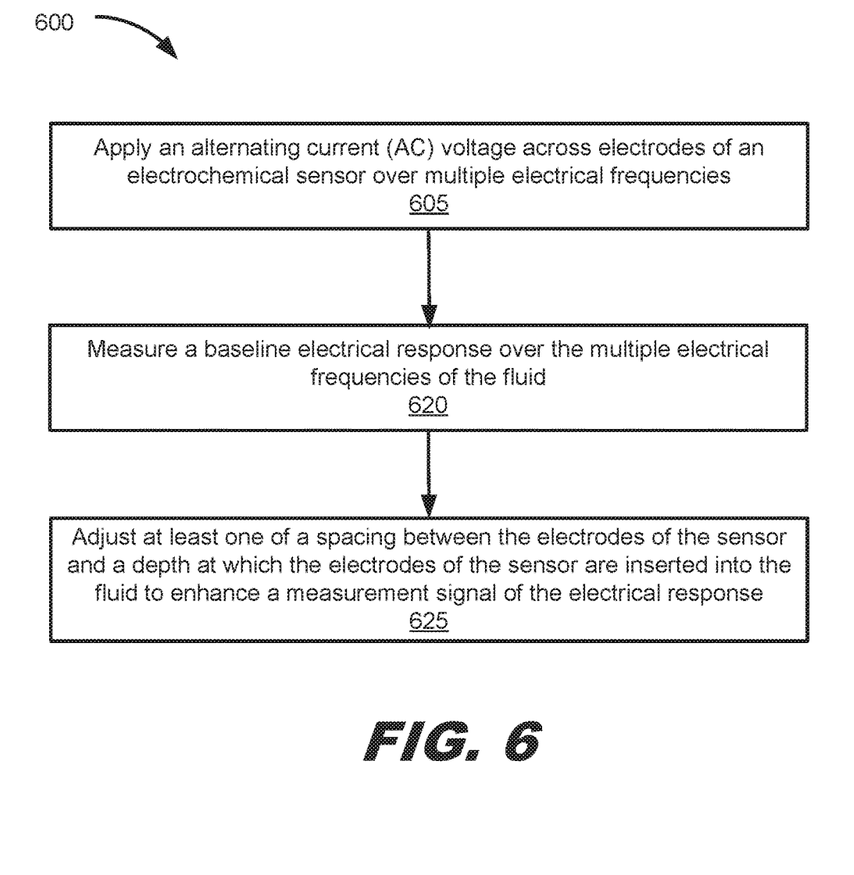
FIG. 6 depicts a flow diagram illustrating another example process of determining whether a chemistry of a fluid is to be adjusted.

FIG. 6 depicts a flow diagram illustrating another example process 600 of determining whether a chemistry of the fluid is to be adjusted.

The process begins at block 605 which may be similar to block 505 described with respect to process 500 of FIG. 5. At block 620, a baseline electrical response of the fluid is measured. The baseline may be taken of fluid that has ideal chemistry for comparison to the fluid having a state of unknown chemistry.

At block 625, at least one of a spacing between the electrodes of the sensor and a depth at which the electrodes of the sensor are inserted into the fluid is adjusted to enhance a measurement signal of the electrical response. For example, if the measurement signal of the electrical response is noisy or not as strong as expected, the spacing between the electrodes may be adjusted to be further apart or closer together to obtain a better signal. Alternatively or additionally, the depth at which the electrodes are inserted into the fluid may be adjusted to be deeper or shallower to obtain a better signal.

Figure 7:
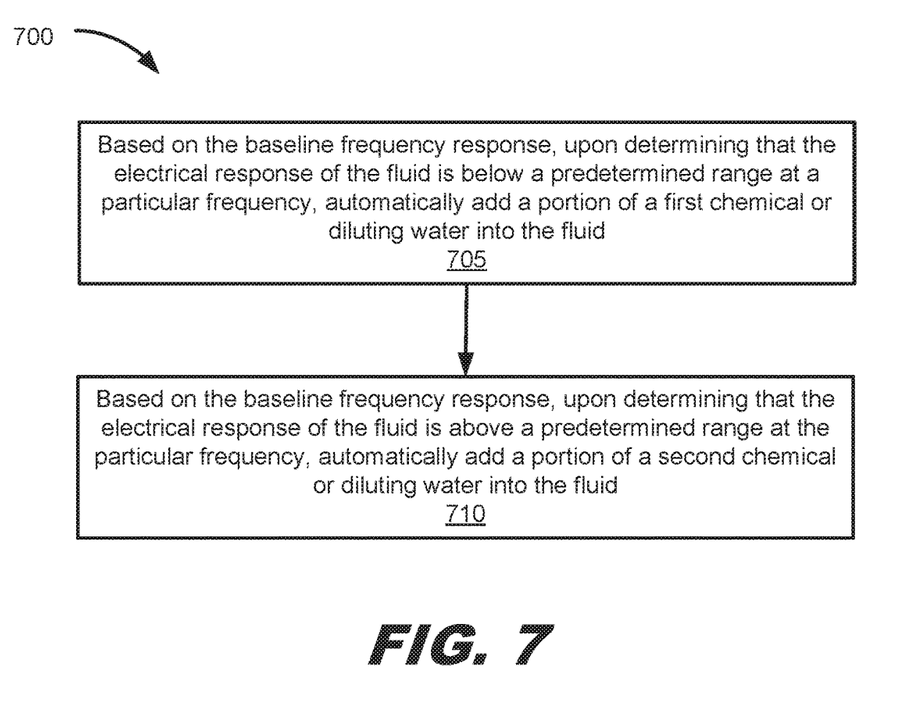
FIG. 7 depicts a flow diagram illustrating another example process of determining whether a chemistry of the fluid is to be adjusted.

FIG. 7 depicts a flow diagram illustrating an example process 700 of determining whether a chemistry of the fluid is to be adjusted. In particular, block 515 of FIG. 5 may involve process 700.

The process begins at block 705, where based on a previously recorded baseline electrical response, upon determining that the measured electrical response of the fluid is below a predetermined range at a particular frequency, a portion of a first chemical or diluting water is automatically added into the fluid. The amount of the first chemical or diluting water to be added may be predetermined.

At block 710, based on the baseline frequency response, upon determining that the chemistry of the fluid is above a predetermined range at the particular frequency, a portion of a second chemical or diluting water is automatically injected into the fluid. The amount of the second chemical or diluting water to be added may be predetermined.

Not all of the steps or features presented above are used in each implementation of the presented techniques. Steps may be performed in a different order than presented.

As used in the specification and claims herein, the singular forms "a," "an," and "the" include plural referents unless the context clearly dictates otherwise.

What is claimed is:

1. A system comprising:
   an electrochemical sensor having two electrodes that, in operation, are inserted into a fluid to be tested, wherein an alternating current (AC) voltage is applied across the two electrodes;
   a potentiostat that, in operation, determines a measured electrical response of the fluid across the two electrodes; and
   a frequency response analyzer that, in operation, analyzes the measured electrical response determined using the two electrodes across multiple frequencies, stores a baseline electrical response across the multiple frequencies, and determines from the baseline electrical response and the measured electrical response whether the measured electrical response is outside a predetermined range.

2. The system of claim 1, further comprising:
   a processor;
   a first reservoir containing a first chemical or diluting water;
   a first injector controlled by the processor to automatically inject a first amount of the first chemical or diluting water into the fluid if the measured electrical response is above the predetermined range;
   a second reservoir containing a second chemical or diluting water; and
   a second injector controlled by the processor to automatically inject a second amount of the second chemical or diluting water into the fluid if the measured electrical response is below the predetermined range.

3. The system of claim 1, wherein the measured electrical response and the baseline electrical response correspond to a pH of the fluid or a concentration of a specific chemical in the fluid.

4. The system of claim 3, wherein the specific chemical includes a biocide or a corrosion inhibitor.

5. The system of claim 1, further comprising a closed loop cooling system, wherein the fluid is in the closed loop cooling system.

6. The system of claim 1, further comprising:
   a controller to:
      adjust a spacing between a first electrode and a second electrode of the two electrodes; and
      adjust a depth at which the first electrode and the second electrode are inserted into the fluid to be tested.

7. The system of claim 1, wherein the stored baseline electrical response is an impedance, a phase difference between current and voltage, or both the impedance and the phase difference between current and voltage.

* * * * *